United States Patent [19]
Weckström et al.

[11] Patent Number: 6,097,034
[45] Date of Patent: Aug. 1, 2000

[54] RADIATION SOURCE ASSEMBLY AND TRANSDUCER FOR ANALYZING GASES OR OTHER SUBSTANCES

[75] Inventors: Kurt P. Weckström; Matti Huiku, both of Helsinki, Finland

[73] Assignee: Instrumentarium Oy, Helsinki, Finland

[21] Appl. No.: 09/024,368

[22] Filed: Feb. 12, 1998

[51] Int. Cl.$^7$ .......................... G01N 21/35; G01N 21/61
[52] U.S. Cl. .................................. 250/495.1; 250/494.1; 250/343
[58] Field of Search .......................... 250/495.1, 493.1, 250/494.1, 343, 339.13, 504 R

[56] References Cited

U.S. PATENT DOCUMENTS

| | | | |
|---|---|---|---|
| 3,745,349 | 7/1973 | Liston | 250/218 |
| 4,692,622 | 9/1987 | Taniguchi et al. | 250/343 |
| 4,914,720 | 4/1990 | Knodle et al. | 250/343 |
| 5,401,966 | 3/1995 | Gray et al. | 250/343 |
| 5,942,755 | 8/1999 | Dreyer | 250/339.13 |

FOREIGN PATENT DOCUMENTS

| | | | |
|---|---|---|---|
| 729 016 | 8/1996 | European Pat. Off. | G01J 3/10 |
| 83103001 | 9/1983 | WIPO | G01J 3/10 |

OTHER PUBLICATIONS

Gregory J. Sharp, Diffractive Optics Shift from Labs to Catalogs, Laser Focus World, pp. 113, Jun. 1997.

*Primary Examiner*—Edward P. Westin
*Assistant Examiner*—Nikita Wells
*Attorney, Agent, or Firm*—Andrus, Sceales, Starke & Sawall

[57] ABSTRACT

A radiation source assembly and transducer incorporating same are suitable for use in measuring spectral absorption properties of a substance to be analyzed, such as a gas. The radiation source assembly has an optical axis. A measuring radiation source provides radiation in the direction of the axis and a reference radiation source provides radiation in the direction of the axis. An optical diffuser is spaced from the radiation sources along the axis. Radiation from the measuring radiation source and radiation from the reference radiation source are applied to the diffuser and the diffuser forms an exiting radiation beam for the assembly from the radiation of the measuring radiation source and reference radiation source. The exiting radiation beam extends along the axis. In at least a portion of a cross-section of the exiting radiation beam taken perpendicular to the axis, the configuration of the distribution of the radiation from each of the sources as seen by a detector in generally the same so that the operation of the radiation source assembly resembles that of a single-path photometer. The transducer further includes the detector for receiving the exiting radiation beam after it has passed through the substance. The assembly and transducer may also include optical collecting and concentrating devices for directing radiation to the detector.

72 Claims, 6 Drawing Sheets

RADIATION SOURCE ASSEMBLY AND TRANSDUCER FOR ANALYZING GASES OR OTHER SUBSTANCES

BACKGROUND OF THE INVENTION

The present invention relates to a radiation source assembly. The radiation assembly includes at least two radiation sources displaced laterally with respect to an optical axis of the assembly and further includes at least one optical diffuser spaced from the radiation sources along the optical axis. The invention also relates to a non-dispersive transducer utilizing such a radiation source assembly and having a radiation detector located to receive the radiation emitted by the radiation sources. The invention finds particular utility in the analysis of gases and gaseous mixtures, although its field of use is not limited to such applications.

The analysis of gases based on non-dispersive infrared absorption, such as the identification of the components of anesthetic and breathing gases and the determination of their concentrations in patient environments, is currently carried out by means of transducers requiring considerable space. Basically there are two types of transducers suitable for such analysis—transducers measuring directly in the mainstream of the patient's breathing circuit and transducers measuring in a small sidestream taken from the breathing circuit.

Sidestream transducers are generally located within a patient monitor, to which gas samples are supplied through a small diameter sampling line. The measurement is made at a distance from the patient so that the transport of the gas samples to the transducer can take a few seconds. This causes a time delay in obtaining the measurement results. It also causes a mixing of consecutive samples, which delays the observation of changes in the measurement results; i.e., an increase of the signal rise time. The advantages of sidestream measurement are the minor importance of transducer size and the short distance between the measurement electronic circuits and the transducer. Corrections to the transducer signal can be easily made, and therefor the concentration readings are usually very accurate and reliable although, as noted above, they are obtained with a delay in signal production and increase of rise time. It is due mainly to these disadvantages of sidestream transducers, that mainstream transducers are becoming more common, particularly in applications where speed and response in the measurement results are important.

Mainstream transducers are connected to the mainstream of the patient's breathing circuit by a special adapter. A mainstream transducer of this kind is described e.g. in U.S. Pat. No. 4,914,720. The transducer comprises a sample chamber or connecting tube, which forms a section of the mainstream channel and which has two opposing windows forming part of a sample chamber. The transducer itself is located outside the windows, so that the transducer's infrared radiation source is directed from the outside toward one of these windows and through the mainstream channel toward the second window, on the outside of which is placed at least one measurement detector with its narrow bandpass filter. Typically two detectors are used, and a second detector makes reference measurements through a narrow bandpass filter operating at another wavelength band, in order to correct e.g. disturbances occurring in the radiation intensity. The electrical signals from the detectors are supplied via electrical lines to a device which calculates the measurement result.

A disadvantage of transducers of this type is the signal's sensitivity to the erroneous absorption caused by water and mucus, which may accumulate on the windows of the sample chamber. By heating the windows of the sample chamber it is possible to avoid the condensation of water, but this practice can not reliably compensate for the shading and spectral effects of mucus. The reason for this is that the reference detector will see the amount of mucus differently than the measurement detector, because the transmission band of the narrow bandpass filter of the reference detector and that of the measurement detector are on different wavelength ranges, so that the radiation which passes through the mucus will pass through these filters in different ways. Further the measurement and reference beams located generally in parallel may actually have a different geometric distribution in the sample chamber and this can cause differences in the measurement and reference signals.

Another mainstream transducer like the mainstream transducer described above is described in the publication HEWLETT-PACKARD JOURNAL September 1981, pages 3–5,; R. J. Solomon —"A Reliable, Accurate $CO_2$ Analyzer for Medical Use." In the described transducer, the measurement accuracy is increased, and particularly the drift of the measurement value is reduced, by modulating the infrared radiation passing through the sample chamber with a rotating disk, in which the filters comprise closed cells containing exactly known gaseous mixtures. For example, in a transducer for measuring carbon dioxide, one of the cells contains carbon dioxide. In a solution of this kind, the measurement geometry and reference geometry are approximately equal, and, due to the optical gas filter, the measurement and reference wavelength bands are also equal, as described in the publication thereby overcoming some of the problems associated with the transducer shown in the '720 patent.

However, a transducer of the kind described in the Hewlett-Packard publication is very complicated, expensive, and very sensitive to mechanical shock etc. Further there can occur wear of the bearings of the filter disk, which increases the unreliability and the service costs of the transducer.

The use of an optical gas filter is known e.g. from U.S. Pat. No. 3,745,349. The transducer described in that patent contains two infrared radiation sources, one of which radiates through the other, so that the radiation from both the first and second infrared sources have exactly the same optical path. Between the infrared sources, i.e. in front of the first source, there is an optical filter, which is based on the optical absorption of gas, and which provides a very narrow absorption band at the wavelength of the absorption band of the gas to be measured. The infrared sources are used alternately, so that a detector placed on the opposite side of the sample chamber as seen from the infrared radiation sources receives alternately a measurement signal from the second source and a reference signal from the first source. The beams of radiation from both sources propagate in the same path and see the water and mucus in the sample chamber approximately in the same way because they are of the approximately same wavelength. This structure eliminates a major part of the disadvantages discussed above.

However, the structure of the transducer in U.S. Pat. No. 3,745,349 has such disadvantages that the proposed structure has not found practical use. If conventional long-lasting miniature incandescent lamps with burning time of thousands or tens of thousand hours are used as infrared radiation sources in the transducer, then, due to their slowness, only a very slow alteration of the radiation sources, i.e. a slow modulation, can be realized. The measurement speed achievable with the transducer will not be sufficient. On the other hand, if the filaments are made thinner and smaller to an extent that a sufficiently rapid modulation is possible, the filaments will burn out very quickly, so that the transducer has very low practicality. Errors are also caused by the fact that the filaments have a rather large area in the radiation propagation direction, so that the second gas measurement radiation source shades the first reference radiation source and causes different paths for the beams at the sample chamber and its windows. Moreover, the transducer is so bulky that it can be used only as a sidestream transducer. Therefore the transducer presented in the patent incorporates a fixed sample chamber, and thus is not suited for use on a mainstream transducer, for instance.

An embodiment is also presented in which the second source is not required to transmit the energy received from the first source. This is advantageous from production standpoint and the signal from the first source will also be higher. An optical combining network comprising two intersecting tubes through which the radiation is directed guides the radiation from each source into the sample chamber. However, the described arrangement would have to be very long for the radiation from both sources not to propagate differently through the sample chamber and its windows. This also means that a small reliable transducer cannot be produced in this manner to fulfill the requirements of a mainstream transducer.

BRIEF SUMMARY OF THE INVENTION

The object of this invention is to provide an improved radiation source assembly, particularly an assembly emitting infrared radiation. The assembly is suitable for use in an analysis transducer, such as one for the analysis of gas components by a non-dispersive infrared absorption method, and comprises a radiation source emitting a measurement radiation beam and a radiation source emitting a reference radiation beam.

Another object of the present invention is to provide such a radiation source assembly, in which the output paths of the measurement beam and the reference beam are as identical as possible, whereby their paths in the sample chamber and especially their distribution on each optical surface (normally, windows) of the sample chamber are similar for those portions of the beams that are used for measurement or other purposes.

A further object of the invention is to provide such a radiation source assembly, in which the wavelength distribution of the reference beam corresponds as exactly as possible to the wavelength distribution of the measurement beam, whereby the effect of any impurities on the optical surfaces of the sample chamber can be eliminated regardless of their nature.

By achieving the foregoing objects, the present invention, employs two radiation sources but resembles a single path transducer, in operation, thereby to exhibit the advantages arising from the use of two sources as well as the advantages of a single radiation path.

Yet another object of the present invention is to provide such a radiation source assembly in which the thermal time constant of both radiation sources is sufficiently short that it is possible to operate both radiation sources at a sufficiently high frequency that reliable and accurate measurement results can be obtained from a gaseous mixture changing at least in a patient's breathing rhythm, typically 10–25 Hz. To this end, the modulation frequency can be at least a multiple of the breathing frequency.

A still further object is to provide a transducer, which utilizes the aforesaid radiation source assembly and a detector, and which is sufficiently small as to permit use as a mainstream transducer. The transducer contains no moving parts and is inexpensive to manufacture, reliable, and has a long life-time.

Briefly, the present invention achieves the foregoing and other objects by providing a radiation source assembly and transducer incorporating same suitable for use in measuring spectral absorption properties of a substance to be analyzed, such as a gas. The radiation source assembly has an axis typically forming the optical axis of the assembly and transducer. A measuring radiation source provides radiation in the direction of the axis and a reference radiation source also provides radiation in the direction of the axis. In one embodiment of the invention, the radiation sources are both laterally displaced from the axis and preferably symmetrically arranged with respect to the axis. To this end, the measuring and reference radiation sources may each comprise a plurality of part source components arranged with respect to the axis, for example in a checkerboard pattern, as circumferentially spaced arcuate segments, or as a plurality of parallel strips. In another embodiment of the invention, the sources are arranged coaxially with the axis.

An optical diffuser is spaced from the radiation sources along the axis. Radiation from the measuring radiation source and radiation from the reference radiation source are applied to the diffuser and the diffuser forms an exiting radiation beam for the assembly from the radiation of the measuring radiation source and reference radiation source. The exiting radiation beam extends along the axis. In at least a portion of a cross-section of the exiting radiation beam taken perpendicularly to the axis, the configuration of the distribution of the radiation from each of the sources is, as for example, seen by a detector, generally the same so that the operation of the radiation source assembly resembles that of a single-path photometer.

The optical diffuser may comprise a means, such as a ground glass or plastic plate, a plate having micro prisms or micro lenses on one or both surfaces, or a plate of internally diffusing material.

The transducer further includes a detector for receiving the exiting radiation beam after it has passed through the substance. The assembly and transducer may also include optical collecting and concentrating means for directing radiation to the detector.

The assembly and/or transducer may include optical filters in association with one or both radiation sources and/or the detector.

A significant advantage of the double infrared sources, i.e. the radiation source assembly according to the invention, is that they can be made very small, fast, long-lasting, and reliable. So called micro-mechanics can be used in the manufacturing of the double radiation sources in order to achieve this, whereby the dimensions of each radiation source can be of the order from a few tens or hundreds micrometers to a few millimeters. The time constant of the radiation sources can be made short due to the small thermal mass of the sources. The wavelength distribution of the radiation sources is chosen so that the measurement source reacts to the absorption in the medium under examination whereas that of the reference source reacts minimally or not at all. This can be accomplished either using specific narrow bandpass filters or by using a gas cavity, filled preferably with the type of gas to be measured, in front of the reference source.

According to the invention, combination of the radiation of the two closely spaced radiation sources is achieved by using at least one optical diffuser and preferably also by splitting each radiation source into smaller part source components located around an optical axis of the radiation source assembly using translation, rotation, inversion from one source type to another, or by using optical means such as mirrors. A very compact double radiation source assembly is obtained when the radiation sources are integrated in proximity on a single chip. When required, a radiation source assembly of this type can be easily mounted in a TO-5 package, well-known e.g. in the semiconductor industry, or in another similar package. The double source assembly can be combined to form a mainstream gas transducer, by adding a sample chamber in front of the radiation source assembly for the gas to be examined, and a detector provided with a narrow bandpass filter corresponding to the wavelength distribution of the absorption band of the medium and the wavelength distribution of the reference region under examination.

BRIEF DESCRIPTION OF THE SEVERAL VIEWS OF THE DRAWING

The invention will be further understood by reference to the following detailed description taken in conjunction with the drawing, in which.

DETAILED DESCRIPTION OF THE INVENTION

Figure 1A:
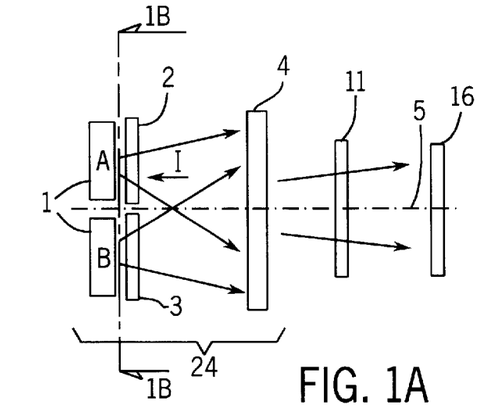
FIG. 1A shows a double radiation source assembly according to the invention in a longitudinal section parallel to the optical axis or main propagation direction of the radiation from the sources.
Figure 1B:
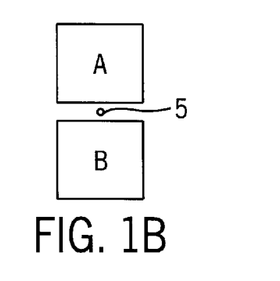
FIG. 1B shows components of the double radiation source assembly of FIG. 1A taken transverse to the optical axis, i.e. along the line 1B–1B of FIG. 1A.

FIGS. 1A and 1B show one embodiment of a double radiation source assembly 24 according to the invention. Double radiation source assembly 24 includes radiation source 1A and radiation source 1B which are laterally displaced from axis 5 of the assembly. Axis 5 typically forms the optical axis of assembly 24 or an orientation axis parallel thereto. The two radiation sources comprise measurement radiation source 1A and reference radiation source 1B. While it is presently deemed preferable to have sources 1A and 1B closely spaced to optical axis 5 and in the same plane perpendicular to optical axis 5, the invention is not limited to such a configuration.

The wavelength region of the radiation emitted from the sources should be adapted to the specific use to which the assembly is put and the optical filters 2 and 3 for sources 1A and 1B, respectively, can be used for this purpose, if necessary. Thus in front of measurement radiation source 1A there can be an optically narrow bandpass filter 2 transmitting radiation absorbed by the gas to be measured. In front of reference radiation source 1B there can be an optically narrow bandpass filter 3 with a wavelength transmission band essentially outside the absorption bands of the gas to be measured. Filter 3 can, for example, be a cell filled with the same type of gas as that to be measured, as described in U.S. Pat. No. 3,745,349. In such a case, filter 2 is not necessarily needed assuming both radiation sources are spectrally broad enough for the intended purpose.

Normally radiation sources 1A and 1B are, at least in the wavelength region of interest, more or less perfect blackbody radiators, e.g. incandescent sources. They can be e.g. miniature lamps but a preferable source is micromechanically produced, such as those described in publication EP-96301174.7 (U.S. Pat. No. 5,668,376). The so called silicon micro-machining technique has become common in recent years, and has made it possible to fabricate different micro-mechanical components having details with dimensions on the order of micrometers. In this technique, related to the methods used in manufacturing of semiconductors, different structures are made in a silicon crystal directly by etching, e.g. with the aid of different protecting masks, or by growing different thin films on the surface of the silicon crystal by vaporizing, sputtering, printing or another technique known from the manufacturing of integrated circuits, the so called thin-film technology. The individual narrow filaments can be formed and protected against oxidizing and their emissivity can be made high, thereby widening the wavelength emission region to different parts of the infrared light region, lowering the necessary working temperature, and increasing the service life. The sources can be closely spaced in the same lateral plane as is presently preferred.

Figure 12A:
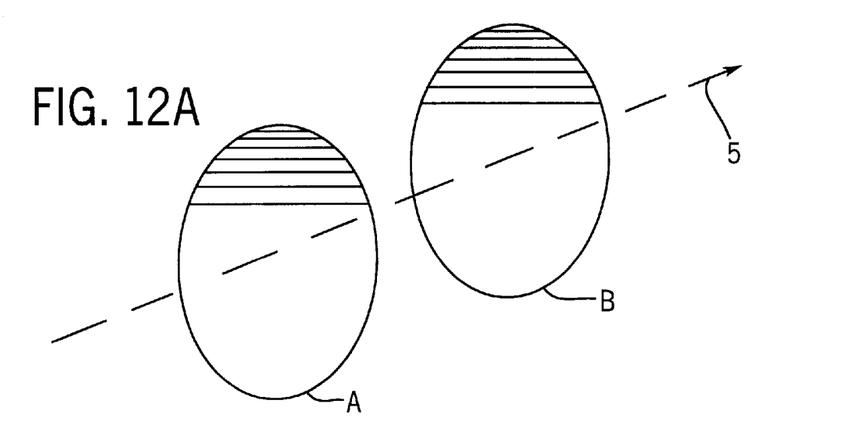
FIGS. 12A and 12B are diagrammatic showings of the cross-section of radiation beams employed in the assembly/transducer of the present invention.
Figure 12B:
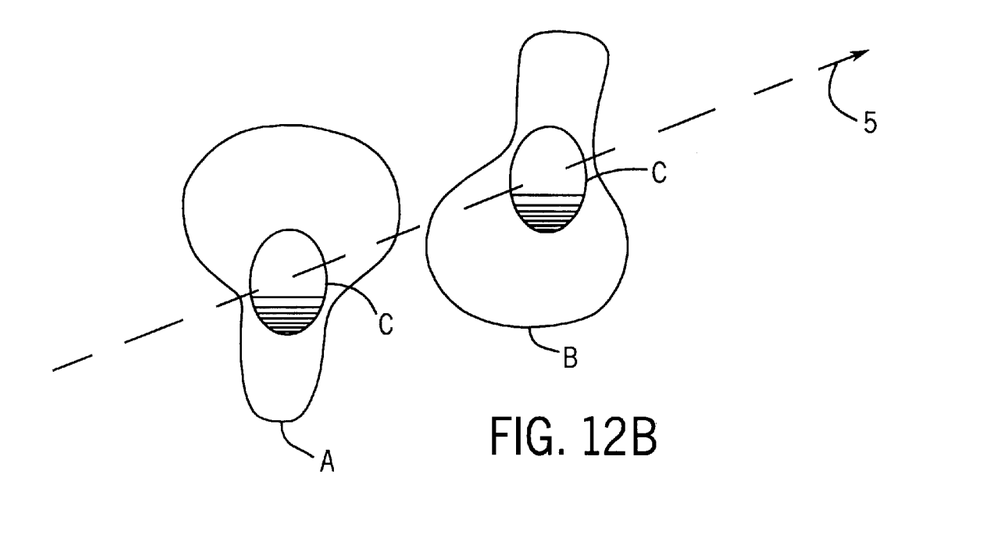

The radiation from both sources 1A and 1B is applied to an optical diffuser 4, spaced from sources 1A, 1B along the optical axis 5, before exiting the source assembly 24. Optical diffuser 4 may be plate-like in form. Diffuser 4 alters, or diffuses, the radiation applied to the diffuser from each of radiation sources 1A and 1B such that one source's radiation, or at least a portion thereof, exiting the diffuser is the same as the other source's radiation, or a portion thereof, exiting the diffuser, when viewed by a detector, such as detector 16, in a cross section taken cross-wise to the optical axis 5. The foregoing is shown in a highly schematic form in FIG. 12. FIG. 12 shows the cross section A of the radiation from radiation source 1A as separated from the cross section B of the radiation from radiation source 1B along the optical axis 5, for ease of explanation. It will be appreciated that, in reality, the optical paths of the exiting radiation are the same and if radiation sources 1A and 1B were operated simultaneously, the radiation of one source would be superimposed on the radiation of the other source on detector 16. FIG. 12A shows an example in which the configuration of the radiation cross sections A and B are the same as seen by detector 16. It is to be understood that an even distribution of the radiation over the cross sections is not required, only that the distribution of radiation in each cross section be the same. With similar cross sectioned radiation patterns A and B, dirt or mucus on one or both of windows 11 and 13, of gas sample chamber 12, shown in FIG. 8, will affect the radiation from both sources equally, reducing measurement errors arising from such causes. FIG. 12B shows a circumstance in which the radiation cross sections $A_1$ and $B_1$ differ but each contain a portion C in which the radiation distribution is the same as seen by detector 16. Portion C can be defined by the geometry of detector 16, or by an aperture device along optical axis 5 as for example, applied to window 11 shown in FIG. 7. While the cross sections A and B are shown as perpendicular to optical axis 5 in FIGS. 12A and 12B, it will be appreciated that the foregoing analysis can be carried out with cross-sections tilted with respect to optical axis 5.

Figure 13A:
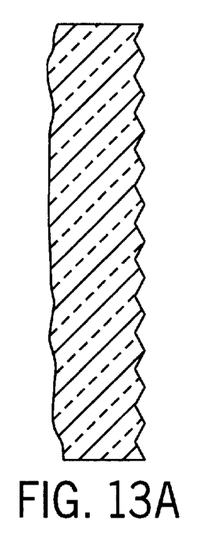
FIGS. 13A through 13E are enlarged, partial, cross-sectional views showing alternative constructions of the optical diffuser element incorporated in the double radiation source assembly of the present invention.
Figure 13B:
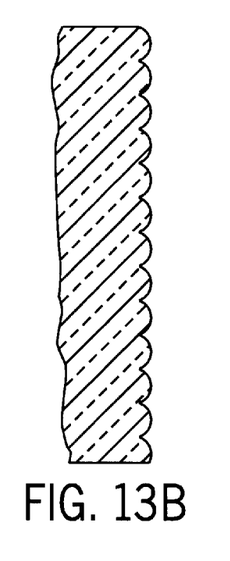
Figure 13C:
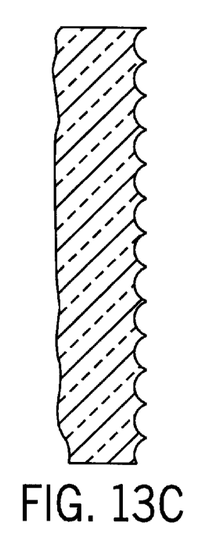
Figure 13D:
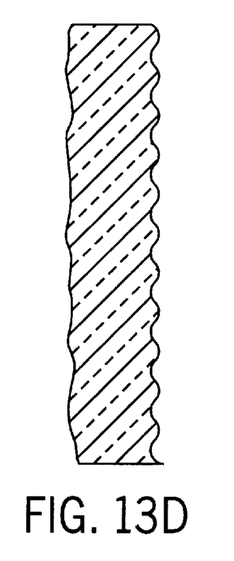
Figure 13E:
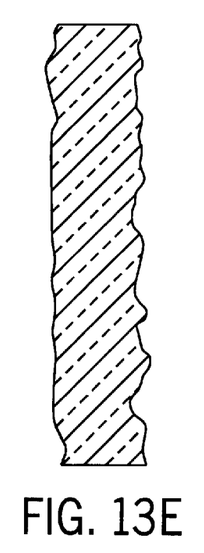

As noted above, the purpose of optical diffuser 4 is to spread out the radiation coming from radiation sources 1A and 1B so that the cross-sectional radiation distribution, or a portion thereof, from the two radiation sources is the same. This may be accomplished by changing the direction of the incoming radiation by an angle within a range characteristic of the specific diffuser. The diffuser can be a ground plate of a material transmissive to the radiation employed in assembly 24, e.g. a ground glass plate, whereby the angular scattering of the incoming radiation is about ±10°. Or diffuser 4 can be a plate structured randomly (FIG. 13E) or using microlenses or microprisms on one or both surfaces of plate-like diffuser 4, as shown in FIGS. 13A through 13D. Diffusers with structured surfaces are manufactured e.g. by Fresnel Technologies, Inc. of Forth Worth, Tex. and by Rochester Photonics Corp. of Rochester, N.Y. With a diffuser 4 using microlenses or microprisms the angular distribution can be chosen to be anything up to that of a Lambertian source with even distribution in all directions. However, with too wide an angular spread, much radiation will not reach the detector 16 and is thus wasted. Thus, for practical cases a scattering angle of about ±30° may be considered an upper limit.

Diffuser plate 4 could also be an internally diffusing material like white quartz or alumina or it could be some form of diffractive optics as described in the publication Laser Focus World, June 1997, page 113. The important thing is that the cross sectional radiation distribution from both sources 1A and 1B as seen by detector 16 is generally the same when applied to window 11.

While diffuser 4 is shown as a flat plate in the Figures of the drawing, it will be appreciated that it may be formed as a curved plate, or some other configuration, if desired.

In FIG. 1B, the individual, closely spaced radiation sources 1A and 1B are not symmetrically located relative to the optical axis 5, i.e. one is above the optical axis, the other is below the optical axis. Only the central parts of diffuser plate 4 will give a cross sectional radiation distribution which is generally the same for both sources for the portion viewed by detector 16.

Figure 2:
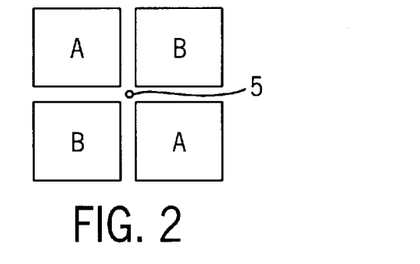
FIG. 2 to 6 show alternative radiation source component arrangements according to the invention, viewed in the same direction as FIG. 1B.
Figure 3:
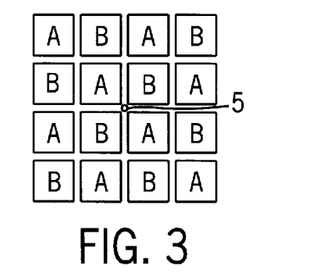

To provide a larger cross sectional area in which the radiation distribution is generally the same, radiation sources 1A and 1B can, in effect, be split. Preferably this source splitting is performed around an axis of symmetry, typically the optical axis 5, but for smaller cross sectional areas this is not necessary. A simple form of source splitting is shown in FIG. 2 in which each source has been split into two diagonally positioned part source components, $1A_1$, $1A_2$; $1B_1$, $1B_2$. It will be appreciated that the resulting source pattern has axial symmetry relative to the optical axis 5, which is a preferred, but not essential configuration. The source components are drawn as squares but could have any appropriate form. In a practical embodiment of radiation source assembly 24, the source components could comprise two crossed filaments. It is recognized that if the filaments are coiled, the axial symmetry is, strictly speaking, not valid but in practice the two parts of each source are still confined within approximately equal areas represented by the squares in FIG. 2 so that as a practical matter such sources can be considered symmetrical. If optical filter 2 and/or 3 are to be used in front of the sources, the structure in FIG. 2 is simple enough for practical constructions. The sources 1A, 1B may be further divided into several smaller part source components, in the checkerboard-like pattern shown in FIG. 3, resulting in the potential for enhancing the performance of assembly 24 but at a possible increase in cost and complexity. The structure of FIG. 3 also possesses axial symmetry and the pattern can be produced by duplicating the pattern of FIG. 2 and making appropriate translations and/or rotations.

Figure 4:
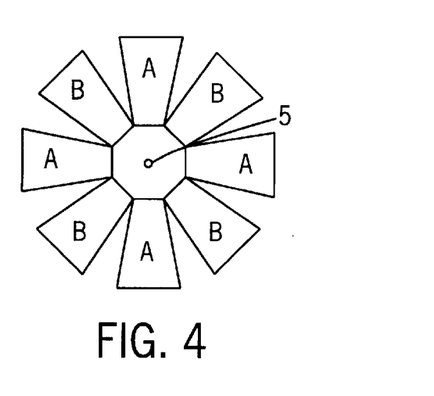
Figure 5:
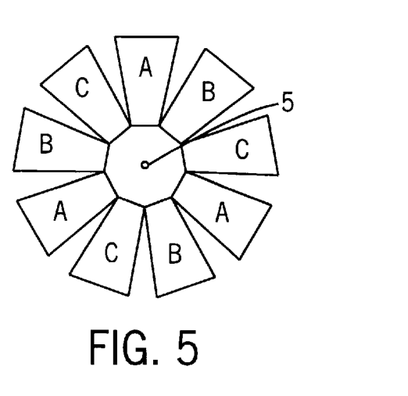

In FIG. 4, axial symmetry is produced using arcuately spaced, alternating part source components $1A_1$, $1B_1$, $1A_2$, $1B_2$, etc., the part source components of source 1A being spaced 90° from each other. The same is true of the part source components of source 1B. Another axial symmetry configuration is shown in FIG. 5 where arcuate displacement by a multiple of 120° of each of the part source components of each source 1A, 1B has been used. In this case, a third source 1C has been added and the angular rotation from one part source component to the next is 40°, not half the repetition angle as with the two sources shown in FIG. 4. The example of FIG. 5 shows that additional sources can be used according to this invention even if two sources are normally used. The use of multiple sources, such as third source 1C, permits use of a different spectral bandwidth, a use of further sampling chamber, etc. and other advantages.

Figure 6:
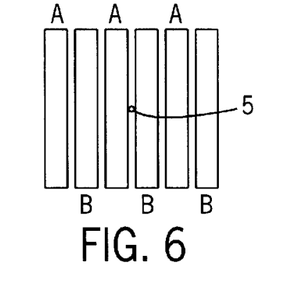
Figure 15:
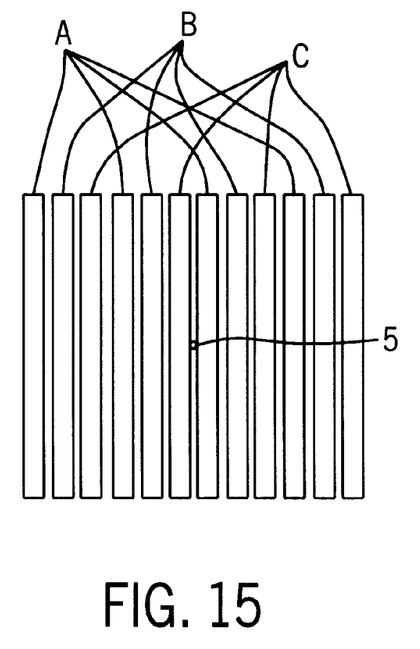
FIG. 15 shows an embodiment of the invention similar to FIG. 6 but with the addition of a further radiation source.

In FIG. 6, the source pattern is produced using a set of elongated, strip-like part source components $1A_1$, $1B_1$, $1A_2$, $1B_2$, etc. This structure works better, for example than that shown in Figure 1B, because the individual sources have been divided into several smaller elongated part source components. FIG. 15 shows a source pattern similar to that of FIG. 6, but with the addition of a third source 1C.

Figure 14A:
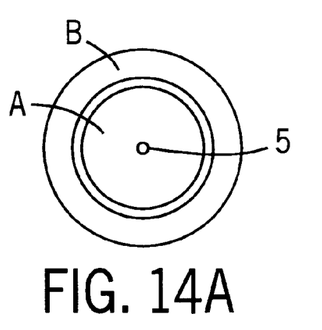
FIGS. 14A and 14B show embodiments of the invention in which the radiation sources are arranged coaxially.
Figure 14B:
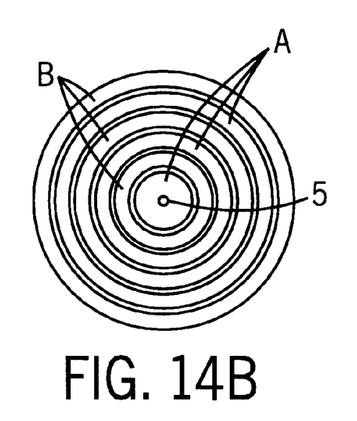

Still further embodiments of the radiation sources are shown in FIGS. 14A and 14B in which the radiation sources, and component parts thereof, are arranged around the axis in a coaxial manner.

It will be appreciated that the smaller and more numerous the part source components, the better is the approximation of symmetry and the better is the mixing of the radiation from the different sources. However it must be recognized that with optical filters, such as 2,3 in front of the part source components, such solutions may, however, be more difficult and expensive to manufacture because of the corresponding complexity in the filter structure.

Figure 7:
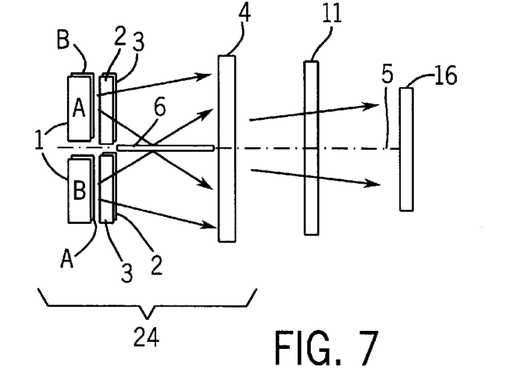
FIG. 7 shows a second embodiment of a double radiation source assembly in a longitudinal section parallel to the optical axis.

A further technique for obtaining a similar cross-sectional distribution pattern in the radiation from sources 1A and 1B is to use mirror images of the sources, so called virtual sources. Such a technique is shown in FIG. 7 which is a view similar to FIG. 1 but schematically showing a source structure of FIG. 2 having part source components $1A_1$ and $1B_1$ above axis 5 and part source components $1B_2$ and $1A_2$ below axis 5. A plane, two-sided mirror 6 is placed along optical axis 5 so that radiation from both sources can be at least partly reflected from each surface of the mirror. As can be seen from FIG. 7, due to the reflection from mirror 6, radiation from the upper part source component $1A_1$ appears to radiate from the lower part source component $1B_2$. This means that a virtual partial source for radiation source $1A_1$ has been created at the location of part source component $1B_2$, and vice versa, thus optically creating a virtual translation of the part source component to the other side of mirror 6 and optical axis 5. It should be noted that use of a fully reflective mirror 6 does not work with the source assembly 24 shown in FIG. 1 because, despite the existence of a virtual source for source 1A at the position of source 1B, all radiation from source 1A would be confined in a space above mirror 6 and, similarly, all radiation from source 1B would be confined in a space below mirror 6. With a fully reflective mirror, it is thus a requirement that both sources 1A, 1B or components of both sources 1A and 1B must be located on the same side of the mirror. With symmetrical sources or those having well divided part source components, such as shown in FIG. 6, or with the use of a partially reflective mirror, the use of a mirror and the resulting virtual images will facilitate obtaining similar cross-sectional distribution patterns in the radiation from sources 1A and 1B.

Figure 8:
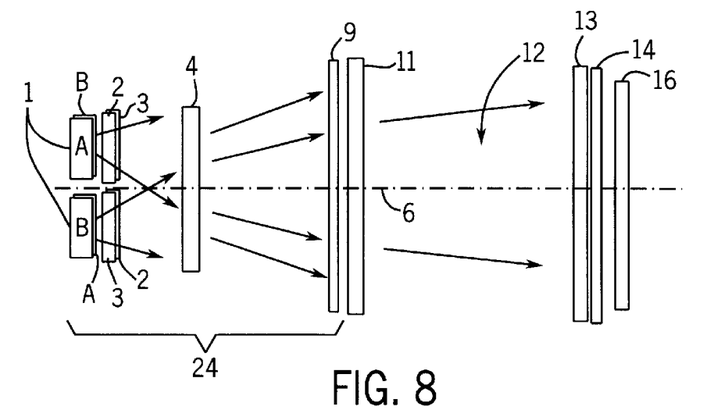
FIG. 8 shows, in a longitudinal section, a transducer according to the invention incorporating a double radiation source assembly.

FIG. 8 shows a transducer incorporating radiation source assembly 24 in which the measuring and reference radiation sources include part source components arranged in the manner shown in FIG. 2. Radiation source assembly 24 incorporates two diffusers 4 and 9 in order to form the same cross sectional radiation distributional pattern for the radiation from sources 1A and 1B. Preferably diffuser 4 near the sources has a wider scattering angle than diffuser 9. Diffuser 4 may have a scattering angle of about ±30° and diffuser 9 may have a scattering angle of about ±10°. This will create a radiation distribution pattern which is generally the same for both sources as viewed by detector 16. The transducer of FIG. 8 is shown in connection with windows 11 and 13, between which the substance, such as a gas sample, being measured is confined in space 12. The radiation distribution patterns from sources 1A and 1B on window 11 do not have to be, and may not be, identical to those on window 13, but the radiations from both sources behave similarly on each window so that the result is that of a single path for the detected radiation. The problems associated with dirt, mucus, condensed water, or other absorbing materials on the windows are thus correctly compensated for.

The transducer shown in FIG. 8 also includes a narrow bandpass filter 14 that limits the wavelength region of the radiation to that relevant for both sources and at the same time it blocks possible ambient disturbing radiation. If the gas to be measured is carbon dioxide and a filter 3, associated with reference radiation source 1B and filled with an appropriate amount of carbon dioxide, is used to establish the radiation band of the reference radiation, then filter 2 is not needed in connection with measuring radiation source 1A. For carbon dioxide measuring, filter 14 is transmissive for a narrow wavelength band at about 4.26 µm.

The transducer further includes detector 16, preferably a lead selenide detector, because of its quick response time. As radiation sources 1A and 1B are normally used alternatingly, only one detector 16 is necessary to obtain signals from both sources. If for example, the breathing of a patient has to be reliably sampled, pulses of radiation from each radiation source must be generated in sequence at least five times per second. This means detector 16 must be able to resolve pulses occurring at a frequency of at least 10 Hz.

Figure 9:
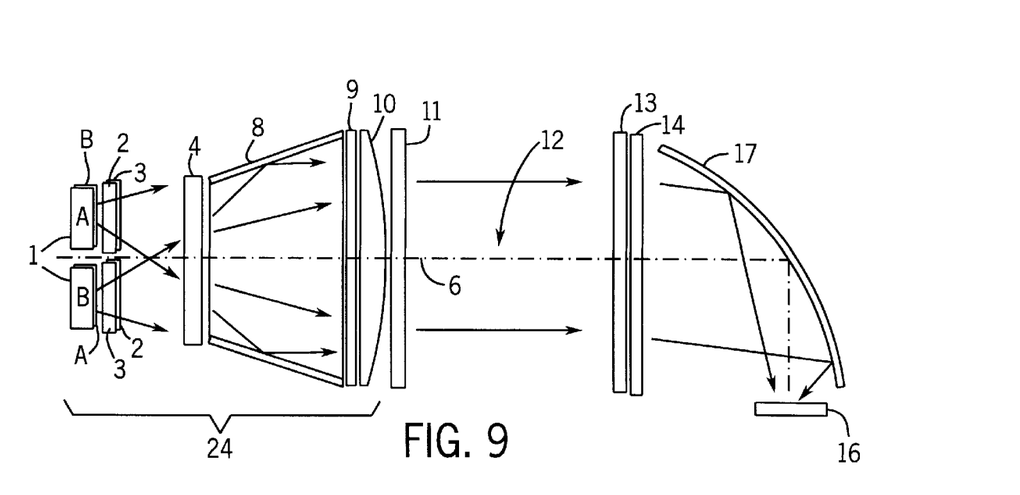
FIGS. 9 and 10 show alternative transducers according to the invention in longitudinal section.

The amount of radiation from sources 1A and 1B seen by the detector in the transducer construction of FIG. 8 may in some cases be too small for reliable noise-free, gas measurement. This can be overcome by the use of optical collecting and concentrating components, a number of which are shown in FIG. 9. FIG. 9 shows the same basic structure as shown in FIG. 8. On the radiation source side of the sample space 12, a cone shaped reflector 8 has been placed between diffusers 4 and 9 thus reflecting parts of the peripheral radiation to second diffuser 9. A positive lens 10 close to diffuser 9 acts as a field lens, further collimating the radiation through the first window 11 and the second window 13 of the sample area 12. Comparably good radiation patterns over a large cross-sectional area are obtained in such a case. To collect the radiation on the detector 16, an off-axis parabolic mirror 17 may used, since detectors big enough to receive all the collimated radiation are expensive or otherwise lack feasibility or availability.

Figure 10:
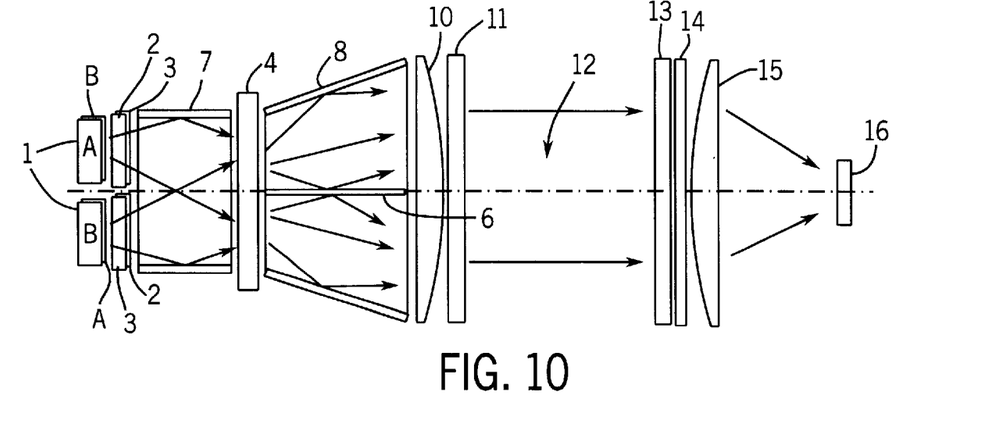

FIG. 10 shows another alternative embodiment of the transducer of the present invention. The embodiment uses radiation sources of the type shown in FIG. 2. A cylindrical reflector 7 is placed between sources 1A and 1B and diffuser 4 and, like the reflecting cone shaped mirror 8, will reflect back part of the peripheral radiation from the sources 1A and 1B in a direction toward detector 16. A plane double-sided mirror 6 is introduced after the diffuser 4 inside the cone shaped mirror 8. By creating virtual images of the sources, as described above, mirror 6 helps to establish a similar cross-sectional radiation pattern for the radiation of each source. A second diffuser, such as diffuser 9, is not necessarily needed in this embodiment. Similar to the embodiment of FIG. 9, a lens 10 collimates the radiation through the window 11 into the sample space 12 and further through the window 13 and optical filter 14 toward lens 15, which focuses the radiation on the detector 16. The function of lens 15 is similar to that of parabolic mirror 17. In the infrared light region, a lens often either absorbs radiation, or without expensive anti-reflective coatings, transmits less radiation than a mirror reflects. On the other hand, a mirror of the off-axis parabolic type may be more expensive than a lens.

Figure 11:
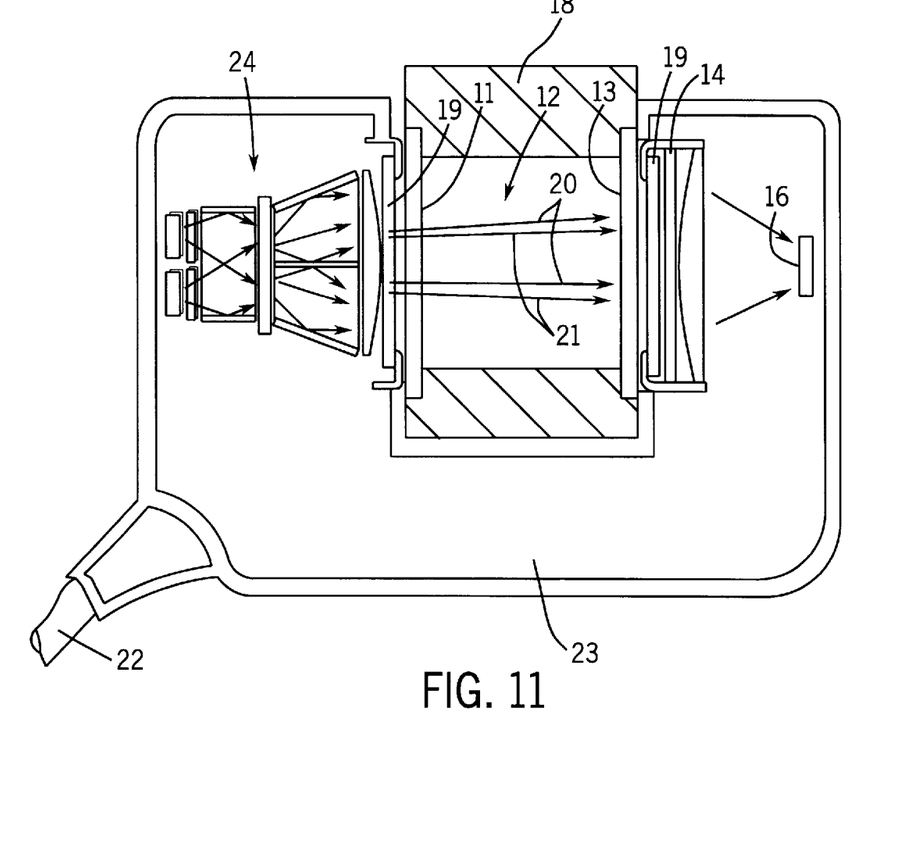
FIG. 11 shows the transducer in FIG. 10 in a mainstream gas analyzer.

FIG. 11 shows the transducer of FIG. 10 incorporated in a typical mainstream gas sensor adapted to measure carbon dioxide. Radiation source assembly 24 and detector 16, and the associated components of each are located in body 23 of the gas sensor on either side of a detachable sample adapter 18 having sample windows 11 and 13. If necessary, protective windows 19 can be mounted in body 23 adjacent to sample adapter windows 11 and 13. The detected radiation beam 20 from the measurement source 1A and the detected radiation beam 21 from the reference source 1B, shown as displaced from each other for exemplary purposes, will alternately both pass through the sample space 12 of the sample adapter 18 and its windows 11 and 13 in similar manner. This means that their background corrected signal ratio calculated from the signals alternatingly generated by the detector 16 and transmitted through a cable 22 to a monitor, as described in detail in the publication EP-96301174.7 (U.S. Pat. No. 5,668,376), will be insensitive to possible dirt, mucus, water or other absorbing material on the windows 11 and 13 and the transducer will work as a single-path photometer.

Other transducer and source assembly alternatives are within the scope of this invention and it will be apparent that many other variations are possible for making a single-path photometer using two or more adjacent radiation sources and at least one optical diffuser.

It is claimed:

1. A radiation source assembly suitable for use in measuring spectral absorption properties of a substance to be analyzed, said radiation source assembly having an axis and comprising:

a measuring radiation source providing radiation along the direction of the axis;

a reference radiation source providing radiation along the direction of the axis; and an optical diffuser spaced from said radiation sources along the axis and to which radiation from said measuring radiation source and radiation from said reference radiation source are applied, said optical diffuser forming an exiting radiation beam for said assembly from the radiation of said measuring radiation source and the radiation of said reference radiation source, said exiting radiation beam extending along the axis, and in said at least a portion of radiation beam, as seen in a cross-section taken cross-wise to the axis, the configuration of the distribution of the radiation from each of said sources is generally the same so that said at least portion of said radiation beam may be used for measurement purposes.

2. A radiation source assembly according to claim 1 wherein said optical diffuser is further defined as forming an exiting radiation beam in which the distribution of the radiation from each of said sources is generally the same over generally all of the cross section of the exiting radiation beam used for measurement purposes.

3. A radiation source assembly according to claim 1 wherein said optical diffuser is further defined as forming an exiting radiation beam in which the distribution of the radiation from each of said sources is generally the same over a portion of the cross section of the exiting radiation beam used for measurement purposes.

4. A radiation source assembly according to claim 1 wherein said optical diffuser is further defined as plate-like optical diffuser.

5. A radiation source assembly according to claim 1 wherein said optical diffuser forms the exiting radiation beam by changing the direction of the radiation applied to the diffuser by said radiation sources.

6. A radiation source assembly according to claim 5 wherein said optical diffuser is further defined as angularly scattering the applied radiation up to about ±30°.

7. The radiation source assembly according to claim 1 wherein said optical diffuser has a ground surface transverse to the axis of said assembly.

8. A radiation source assembly according to claim 5 wherein said optical diffuser comprises a refractive means.

9. A radiation source assembly according to claim 8 wherein said optical diffuser has a plurality of microprisms or microlenses on at least one surface transverse to the axis of said assembly.

10. A radiation source assembly according to claim 1 wherein said diffuser is formed of an internally diffusing material.

11. A radiation source assembly according to claim 1 wherein at least one of said radiation sources is displaced from said axis.

12. A radiation source assembly according to claim 11 wherein both said radiation sources are displaced from said axis.

13. A radiation source assembly according to claim 11 wherein one of said radiation sources contains said axis.

14. A radiation source assembly according to claim 12 wherein said measuring radiation source and said reference radiation source each comprise a radiation source element, one of said radiation source elements being laterally displaced from the axis on one side of the axis, the other of said radiation source elements being laterally displaced from the axis on the other side of said axis.

15. A radiation source assembly according to claim 1 wherein at least one of said radiation sources comprises a plurality of part source components.

16. A radiation source assembly according to claim 15 wherein both of said radiation sources comprise a plurality of part source components.

17. A radiation source assembly according to claim 16 wherein said part source components are arranged in a checkerboard-like pattern.

18. A radiation source assembly according to claim 16 wherein said part source components comprise a plurality of strip-like components.

19. A radiation source assembly according to claim 18 further including an additional radiation source having a plurality of strip-like part source components.

20. A radiation source assembly according to claim 16 wherein the part source components of each of said radiation sources are arcuately spaced about the axis.

21. A radiation source assembly according to claim 20 further including an additional radiation source having a plurality of part source components arcuately spaced about the axis.

22. A radiation source assembly according to claim 15 wherein said radiation sources are arranged coaxially with said axis.

23. A radiation source assembly according to claim 22 wherein at least one of said radiation sources comprises a plurality of part source components arranged coaxially with said axis.

24. A radiation source assembly according to claim 16 further including a two sided mirror for reflecting the radiation of said radiation sources to create corresponding virtual sources and wherein part source components of each of said radiation sources are positioned on each side of said mirror.

25. A radiation source assembly according to claim 1 further including a partially reflective mirror for reflecting and transmitting the radiation of said radiation sources.

26. A radiation source assembly according to claim 1 further including at least one mirror, at least partially surrounding said axis.

27. A radiation source assembly according to claim 24 further including at least one mirror, at least partially surrounding said axis.

28. A radiation source assembly according to claim 25 further including at least one mirror, at least partially surrounding said axis.

29. A radiation source assembly according to claim 1 wherein said measuring radiation source lie generally in the same plane which is transverse to the axis.

30. A radiation source assembly according to claim 1 wherein said measuring and reference radiation sources include lamps.

31. A radiation source assembly according to claim 1 wherein said measuring and reference radiation sources comprise micro-machined components.

32. A radiation source assembly according to claim 1 wherein the measuring radiation source and the reference radiation source provide radiation in the same spectral band.

33. A radiation source assembly according to claim 1 wherein said measuring radiation source and said reference radiation source provide radiation in differing spectral bands.

34. A radiation source assembly according to claim 1 wherein said measuring radiation source is further defined as providing radiation of a wavelength that is absorbable by the substances to be analyzed.

35. A radiation source assembly according to claim 1 wherein said reference radiation source is further defined as providing radiation of a wavelength that is not absorbed by the substances to be analyzed.

36. A radiation source assembly according to claim 34 wherein said reference radiation source is further defined as providing radiation of a wavelength that is not absorbed by the substances to be analyzed.

37. A radiation source assembly according to claim 1 further including an optical filter interposed in the path of the radiation from at least one of said measuring radiation source and said reference radiation source.

38. A radiation source assembly according to claim 37 further including an optical filter interposed in the path of the radiation of both said measuring radiation source and said reference radiation source.

39. A radiation source assembly according to claim 37 wherein said reference radiation source includes an optical filter for establishing the radiation properties of the radiation from said reference radiation source.

40. A radiation source assembly according to claim 39 further defined as suitable for use in measuring spectral absorption properties of gas and wherein said filter of said reference radiation source includes the gas to be measured.

41. A radiation source assembly according to claim 37 wherein an optical filter in the path of the radiation from said measurement radiation source transmits radiation in a band having radiation with a wavelength that is absorbable by the substances to be measured.

42. A radiation source assembly according to claim 37 wherein an optical filter in the path of the radiation from said reference radiation source transmits radiation of a wavelength that is not absorbed by the substances to be analyzed.

43. A radiation source assembly according to claim 1 including a pair of optical diffusers displaced from said radiation sources along the axis.

44. A radiation source assembly according to claim 43 wherein each of said diffusers has different radiation diffusing properties.

45. A radiation source assembly according to claim 44 wherein a diffuser nearer said measuring and reference radiation sources has a wider scattering angle than a diffuser further from said sources.

46. A radiation source assembly according to claim 1 further defined as one for measuring the spectral absorption properties of a gas to be analyzed.

47. A transducer suitable for use in measuring spectral absorption properties of a substance to be analyzed, the substance being retained in a receptacle, said transducer comprising:
a radiation source assembly having an axis and comprising:
a measuring radiation source providing radiation along the direction of the axis;
a reference radiation source providing radiation along the direction of the axis; and
an optical diffuser spaced from said radiation sources along the axis and to which radiation from said measuring radiation source and radiation from said reference radiation source are applied, said optical diffuser forming an exiting radiation beam from the radiation of said measuring radiation source and the radiation of said reference radiation source, said exiting radiation beam being applied to the receptacle for the substance, said exiting radiation beam extending along the axis; and
a detector for receiving radiation exiting from the receptacle,
in at least a portion of said radiation beam, as seen in a cross-section taken cross-wise to the axis, the configuration of the distribution of the radiation from each of said sources as detected by said detector is generally the same.

48. A transducer according to claim 47 wherein said optical diffuser is further defined as forming an exiting radiation beam in which the distribution of the radiation from each of said sources as detected by said detector is generally the same over generally all of the cross section of the exiting radiation beam.

49. A transducer according to claim 47 wherein said optical diffuser is further defined as forming an exiting radiation beam in which the distribution of the radiation from each of said sources as detected by said detector is generally the same over a portion of the cross section of the exiting radiation beam.

50. A transducer according to claim 47 wherein said optical diffuser is further defined as plate-like optical diffuser.

51. A transducer according to claim 47 wherein said optical diffuser forms the exit radiation beam by changing the direction of the radiation applied to the diffuser by said radiation sources.

52. A transducer according to claim 51 wherein said optical diffuser is further defined as angularly scattering the applied radiation up to about ±30°.

53. A transducer according to claim 47 including a pair of optical diffusers displaced from said radiation sources along the axis for providing the exiting radiation beam applied to the receptacle.

54. A transducer according to claim 53 wherein each of said diffusers has different radiation diffusing properties.

55. A transducer according to claim 54 wherein a diffuser nearer said measuring and reference radiation sources has a wider scattering angle than a diffuser further from said sources.

56. A transducer according to claim 47 wherein at least one of said radiation sources is displaced from the axis.

57. A transducer according to claim 56 wherein both said radiation sources are displaced from said axis.

58. A transducer according to claim 47 wherein said radiation sources are coaxial with said axis.

59. A transducer according to claim 47 wherein at least one of said radiation sources comprises a plurality of part source components.

60. A transducer according to claim 59 further including a two sided mirror for reflecting the radiation of said radiation sources to create corresponding virtual sources and wherein part source components of each of said radiation sources are positioned on each side of said mirror.

61. A transducer according to claim 47 further including a partially reflective mirror for reflecting and transmitting the radiation of said radiation sources.

62. A transducer according to claim 47 further including at least one mirror, at least partially surrounding said axis.

63. A transducer according to claim 53 further including at least one mirror at least partially surrounding said axis between said pair of optical diffusers.

64. A transducer according to claim 63 further including at least one mirror lying generally along said axis between said diffusers.

65. A transducer according to claim 47 wherein said measuring radiation source is further defined as providing radiation of a wavelength that is absorbable by the substances to be analyzed.

66. A transducer according to claim 47 wherein said reference radiation source is further defined as providing radiation of a wavelength that is not absorbed by the substances to be analyzed.

67. A transducer according to claim 47 further including an optical filter interposed in the path of the radiation from at least one of said measuring radiation source and said reference radiation source.

68. A transducer according to claim 47 further including an optical filter interposed in the path of the radiation of both said measuring radiation source and said reference radiation source.

69. A transducer according to claim 47 further including a filter interposed in front of said detector.

70. A transducer according to claim 47 further including at least one optical collecting or concentrating component for radiation in said transducer.

71. A transducer according to claim 70 wherein said optical collecting or concentrating means comprises lens means.

72. A transducer according to claim 70 wherein said optical collecting or concentrating means comprises mirror means.

* * * * *